United States Patent [19]

Abela et al.

[11] Patent Number: 5,769,843

[45] Date of Patent: Jun. 23, 1998

[54] PERCUTANEOUS ENDOMYOCARDIAL REVASCULARIZATION

[75] Inventors: George S. Abela, Lansing, Mich.; Russell W. Bowden, Tyngsboro, Mass.

[73] Assignee: CorMedica, Natick, Mass.

[21] Appl. No.: 603,484

[22] Filed: Feb. 20, 1996

[51] Int. Cl.⁶ .................................................. A61B 17/36
[52] U.S. Cl. .............................................. 606/10; 606/15
[58] Field of Search ........................... 128/653.1, 660.03, 128/662.06, 899; 606/6–7, 11, 13–15, 18

[56] References Cited

U.S. PATENT DOCUMENTS

| | | |
|---|---|---|
| 4,176,662 | 12/1979 | Frazer . |
| 4,592,364 | 6/1986 | Pinto . |
| 4,658,817 | 4/1987 | Hardy . |
| 4,693,556 | 9/1987 | McCaughan, Jr. . |
| 4,860,743 | 8/1989 | Abela . |
| 4,913,142 | 4/1990 | Kittrell et al. . |
| 4,936,304 | 6/1990 | Kresh et al. . |
| 4,941,473 | 7/1990 | Tenerz et al. . |
| 5,041,109 | 8/1991 | Abela . |
| 5,056,517 | 10/1991 | Fenici . |
| 5,061,265 | 10/1991 | Abela et al. . |
| 5,109,859 | 5/1992 | Jenkins ............................... 128/662.03 |
| 5,188,635 | 2/1993 | Radtke . |
| 5,201,729 | 4/1993 | Hertzmann et al. . |
| 5,207,103 | 5/1993 | Wise et al. . |
| 5,285,795 | 2/1994 | Ryan et al. . |
| 5,345,940 | 9/1994 | Seward et al. ...................... 128/662.06 |
| 5,377,683 | 1/1995 | Barken ................................ 128/660.03 |
| 5,380,316 | 1/1995 | Aita et al. . |
| 5,389,096 | 2/1995 | Aita et al. . |
| 5,391,199 | 2/1995 | Ben-Haim . |
| 5,423,805 | 6/1995 | Brucker et al. . |
| 5,443,489 | 8/1995 | Ben-Haim . |
| 5,464,404 | 11/1995 | Abela et al. . |
| 5,468,239 | 11/1995 | Tanner et al. . |
| 5,480,422 | 1/1996 | Ben-Haim . |
| 5,496,305 | 3/1996 | Kittrell et al. . |
| 5,496,307 | 3/1996 | Daikuzono . |
| 5,496,309 | 3/1996 | Saadat et al. . |
| 5,546,951 | 8/1996 | Ben-Haim . |
| 5,554,152 | 9/1996 | Aita et al. . |
| 5,558,091 | 9/1996 | Acker et al. ........................ 128/653.2 |
| 5,568,809 | 10/1996 | Ben-Haim . |
| 5,570,671 | 11/1996 | Hickey . |
| 5,592,939 | 1/1997 | Marinelli . |
| 5,607,421 | 3/1997 | Jeevanandam et al. . |

FOREIGN PATENT DOCUMENTS

WO96/05768  2/1996  WIPO .
WO97/25101  7/1997  WIPO .

*Primary Examiner*—Francis Jaworski
*Attorney, Agent, or Firm*—William L. Feeney; Kerkam, Stowell, Kondracki & Clarke, P.C.

[57] ABSTRACT

A system and method for percutaneous myocardial revascularization uses laser energy emitted from the distal end of a catheter. A technique for controlling beam direction allows the creation of channels in a patient's heart tissue with the channels having different orientations relative to the distal end. An arrangement provides for the creation of a plurality of channels at one time by simultaneous application of a plurality of beams of laser energy. A navigation arrangement uses two non-coplanar magnetic sensing coils in the distal end of the catheter cooperating with three sets of three magnetic field generating external coils (i.e., external to the patient). Each of the three sets is sequentially energized and the sensing coils in the distal end sense the magnetic fields established. A computer compares the sensed fields with the known sequence of energizing the external coils and thereby determines the position of the distal end. A pressure sensor in the catheter senses ventricular pressure in the patient's heart during and immediately after revascularization.

35 Claims, 5 Drawing Sheets

PERCUTANEOUS ENDOMYOCARDIAL REVASCULARIZATION

Background of the Invention

The present invention relates to percutaneous endomyocardial revascularization. In other words, it involves use of a device within a patient's heart to create channels other than the coronary arteries, which channels can supply oxygenated blood and remove waste products from the myocardial tissue.

George S. Abela (an inventor herein) is also an inventor on various U.S. Patents and applications, some of which are discussed hereafter.

Prior U.S. Pat. No. 5,464,404 issued Nov. 7, 1995 to George S. Abela (an inventor herein) et al., based on Ser. No. 123,207 filed Sep. 20, 1993, hereby incorporated by reference, discloses a cardiac ablation catheter having an inner portion movable relative to an outer catheter portion. The inner and outer portions are sometimes referred to as an inner catheter and an outer catheter. These portions are rotatable and translatable (i.e., linear movement) relative to each other. The arrangement provides for anchoring a part of the outer portion at an anchor point. The inner portion may then be rotated and translated (moved lengthwise) relative to the outer portion. Additionally, both the inner portion and outer portion of the catheter can be pivoted about the anchor point in a windshield wiper type movement. These three types of movement provide great flexibility in applying laser energy from the catheter to desired locations.

George S. Abela and Stephan E. Friedl obtained U.S. Pat. No. 5,061,265 on Oct. 29, 1991, entitled "LASER TREATMENT APPARATUS AND METHOD", hereby incorporated by reference. That patent discloses a dual hood arrangement whereby laser energy passes out through an inner hood having a window of transparent material and passes through an opening of an outer hood. By supplying pressurized flushing solution to within the outer hood, the flushing solution maintains the inner hood relatively clear of burned materials and flows out the same opening as the laser energy.

Among other prior patents, U.S. Pat. Nos. 4,860,743, issued Aug. 29, 1989 to George S. Abela and 5,041,109, issued Aug. 20, 1991 to George S. Abela, both disclose various laser catheters for treatment of cardiac conditions. Those patents, both of which are hereby incorporated by reference, disclose the use of electrode rings on the catheters for detection of conduction tissue. Such rings are also discussed in the Abela et al '265 patent mentioned above. The electrode rings allow one to locate tissue which is to be treated.

U.S. application entitled "CARDIAC CATHETER ANCHORING AND METHOD", Ser. No. 08/474,462 filed on Jun. 7, 1995 is a continuation-in-part of U.S. patent application Ser. No. 08/123,207 in the names of Abela, Friedl, Mathews, and Bowden. A divisional application Ser. No. 08/394,763 of that application was filed on Feb. 27, 1995. Another continuation-in-part of U.S. patent application Ser. No. 08/123,207 was filed Jun. 7, 1995 as Ser. No. 08/474,152 in the names of Abela, Friedl, and Mathews and is entitled "OPTICAL FIBER CATHETER AND METHOD",. Another continuation-in-part of U.S. patent application Ser. No. 08/123,207 was filed Jun. 7, 1995 as Ser. No. 08/484,895 in the names of Abela, Friedl, Mathews and is entitled "MAPPING CATHETER AND METHOD".

All of the above referenced applications and patents including their claims, drawings and text as originally filed and all amendments made prior to the present filing date are hereby incorporated by reference.

Myocardial infarctions (heart attacks) are the major pathological killer in America, resulting in the deaths of more than 500,000 persons each year. The flow of blood is compromised as atherosclerotic plaques develop within the coronary arteries, constricting their diameter, and quite often death ensues due to the complications inherent with the ischemia or infarction of the myocardium. Despite important advances which have been made in preventing and treating atherosclerotic cardiovascular disease, coronary artery impairments continue to constitute a major health problem. The most pervasive method of treating acute coronary artery occlusions is bypass surgery; however, opening of the thoracic cavity entails great pain, risks for the patient, and high costs.

An alternative to bypass surgery is percutaneous transluminal angioplasty (using balloons, lasers, or a combination), a technique for delivering an object capable of removing lesions from affected arteries via a catheter. A serious side effect is the possible rupture of the blood vessel. Furthermore, there are significant numbers of afflicted individuals who are not candidates for either of these therapeutic procedures for the treatment of myocardial ischemia. These include patients with severe small-vessel diseases, diabetes, and those who could not withstand the trauma of cardiopulmonary bypass. More advanced techniques would be welcome for handling these cases, especially a means for the direct recanalization of the afflicted myocardium.

In the procedure known as balloon angioplasty, a thin catheter which contains at its distal end a tiny deflated balloon is threaded through an artery to the location of blockage. When in place in the region of occlusion, the balloon is inflated, and the obstructing plaque in the blood vessel is compressed against the arterial wall. This procedure is much less costly and traumatic to the patient than coronary bypass surgery. Many patients have been subjected to this therapy, and many of them have been relieved of symptoms. Unfortunately, it is often found that restenosis occurs over time because, basically, nothing has been removed from the artery. Although some patients receive a long term cure, others find that blockage reoccurs in about six months time.

There have been a number of reports of attempts to vaporize atherosclerotic plaque using laser radiation delivered to the site of the occlusion through flexible optical fibers carried within a catheter. While the long-wavelength Er and $CO_2$ lasers may be well suited to the task, there is presently no fiber available that meets transmission specifications and required cost levels. A significant number of laser procedures presently result in either perforation or dissection of the vessel, and restenosis due to wall damage remains a significant cause of failure during long-term follow up.

As an alternative procedure, direct myocardial revascularization can provide a supply of channels other than the coronary arteries to supply oxygenated blood and remove waste products from the myocardial tissue. Because the heart has the ability to use conduits and communicating channels to perfuse itself, several different approaches have been taken for exploring the possibility of direct revascularization of the ischemic myocardium. Techniques of revascularization are disclosed in U.S. Pat. No. 5,061,265 issued to Dr. George S. Abela and hereby incorporated by reference. One revascularization technique attempted to introduce collateral circulation using myopexy (roughening the myocardial surface to enhance capillarization) and omentopexy (sewing the omentum over the heart to provide a new blood supply). Another approach involved implanting the left internal mammary artery directly into heart muscle so that blood flowing through side branches of this artery could perfuse the muscle. The blood was distributed by sinusoids and communicating networks within the myocardium. Similar techniques have involved polyethylene tubes, endocardial incisions, the creation of channels with various types of needles, and needle acupuncture.

The needle acupuncture approach rests on the critical observation that in the hearts of vipers and reptiles, myocardial perfusion occurs via communicating channels between the left ventricle and the coronary arterial tree. Thus there exist central channels in the reptilian heart that radiate from the ventricular cavity and perfuse the thickness of the myocardial wall. Reptiles do not have to rely on the functioning of coronary arteries in the same manner as mammals must. This finding is the central thesis underlying attempts to duplicate the reptilian vascular pattern in the mammalian heart. However, it has been shown that the channels formed by acupuncture all close within two or three months due to fibrosis and scaring. Therefore such mechanical techniques have been largely abandoned in favor of the use of lasers to effect transmyocardial canalization. The most important advantage of channels created by a laser is that there is no mechanical injury to the heart muscle, because the channels are created by vaporization. Reports indicate that in laser canalization, fibrosis and scaring are limited, and the laser-produced channels remain patent for more than two years.

The unique properties possessed by certain types of lasers that can be applied to myocardial revascularization include removal of tissue by vaporization; high absorption of the light wave by biological tissue; rapid vaporization with little thermal damage to surrounding tissue; and precise selection of the tissue to be removed. Studies based on using the $CO_2$ laser to create channels relied on penetration of the wall of the heart by focussing the laser on the epicardium and ablating tissue until the endocardium was breached. Studies on mongrel dogs indicated that a 400 W $CO_2$ laser was able to penetrate through the wall of the heart in microseconds, and that channel size could be controlled by the external optical system. When the canine hearts were later examined, it was found that epicardial sites of the laser channeling were marked by dots of fibrous tissue, which apparently is able to heal the outer surface punctures and prevent chronic bleeding. These plugs only penetrated about one millimeter into the channel, so the revascularization was successful. Early results on human subjects also appear to be promising. However, conventional surgical procedures were required, including opening of the chest cavity and cardiopulmonary bypass.

There are several problems associated with passing laser energy through an optical fiber to reach the heart or any inside part of a patient. If laser energy passes from the proximal end (i.e., input end, outside of patient) to the distal end of an optical fiber catheter within a patient, the laser energy looses some of its coherence. It will spread as a conical beam upon exiting the distal end or tip of the optical fiber. Since its power density distribution drops off with the square of the radius, any tissue offset sufficiently from the tip will be subject to a beam of lower power density. This may result in undesirable burning, charring, and/or heating of the tissue, instead of the ablation of the tissue desired under various circumstances. This may prevent or minimize the effectiveness of a given medical procedure, especially where the spreading or diffusion of the laser beam causes it to strike healthy tissue adjacent to the desired target. In cardiovascular applications, the burning, charring, and heating may inhibit desired growth of vascular tissue at the treated sites.

Another problem with applying lasers internally to a patient is that the wavelengths of light which will pass through a regular optical fiber catheter do not include the wavelength which the body tissues will most readily absorb. Using other wavelengths of light increases the risk that the laser beam energy will puncture the wall of a vessel or other body tissue before the laser energy is completely absorbed. In other words and for example, a laser beam which must pass through 2 millimeters of tissue before complete absorption is more likely to puncture than one which is completely absorbed in 1 millimeter. The relatively slow drop off of power in the beam direction of such less than ideal wavelengths for absorption makes it difficult to precisely control the depth of the ablation or the resulting hole. One can decrease the danger of puncture by reducing the beam power, but this may increase the problem of low power density causing undesirable burning, charring, and/or heating of the tissue, instead of the ablation of the tissue. (Notwithstanding some of these problems, the incorporated by reference '743 disclosed in both its background and its various designs the use of lasers for recanalization, among other uses.)

Recent developments of zirconium fluoride and sapphire fibers have been described as paving the way for possible endoscopic applications of short penetration depth lasers, but use of non-standard optical fibers introduces possible problems. Moreover, such suggestions would still require passage of the treatment beam (i.e., laser beam which actually strikes the patient's tissues) through fibers which cause loss of coherence and beam spreading.

The direct application (i.e., without passage through an optical fiber) of a laser beam to a patient's tissue such as the heart for revascularization avoids the spreading of the beam and associated problems, but requires major surgery such as, in the case of revascularization, opening of the chest cavity. This increases the risk to the patient. In the case of revascularization by transmyocardial canalization, the laser beam is directly applied to the outside of a heart and is used to create a channel extending into the interior of the heart (i.e., a through channel). This causes bleeding and later clotting may or may not significantly block the channel which was formed. Although some early results are promising, there is still a danger that the clotting will negate the benefits of the created channels.

The Aita U.S. Pat. No. 5,389,096, issued Feb. 14, 1995, discloses percutaneous myocardial revascularization, whereas Aita U.S. Pat. No. 5,380,316, issued Jan. 10, 1995, discloses myocardial revascularization by applying a laser beam to create channels from the outside of the heart. Those two patents are hereby incorporated by reference.

Although those and other techniques have been generally useful, supplemental and/or alternate techniques are still quite desirable. In particular, techniques are needed which can provide precise positioning and precise repositioning (i.e., getting the catheter to the same position or an offset position precisely offset position from a previous position). Further, techniques which provide flexibility in creating channels and allow more convenient creation of patterns of channels are desirable. Additionally, techniques which better monitor the heart during myocardial revascularization are desirable.

OBJECTS AND SUMMARY OF THE INVENTION

Accordingly, it is a primary object of the present invention to provide a new and improved catheter and associated method for myocardial revascularization of a patient. (As used herein, a patient may be a human or animal patient.)

A more specific object of the present invention is to provide a catheter and technique for percutaneous endomyocardial revascularization.

A further object of the present invention is to provide revascularization with a high degree of accuracy in positioning of new channels placed in the patient by providing highly accurate positioning and repositioning of a catheter.

Yet another object of the present invention is to provide treatment of diseased tissue of a patient with minimal impact on adjacent tissues.

A further object of the present invention is to provide myocardial revascularization without the need for opening the chest cavity.

Yet another object of the present invention is to provide endovascular myocardial revascularization without having to create a through channel with its associated bleeding and potential for clots damaging its effectiveness.

A further object of the present invention is to provide myocardial revascularization with flexibility in creating channels and/or patterns of channels.

A further object of the present invention is to provide myocardial revascularization with improved monitoring of heart conditions.

The above and other features of the present invention which will be more readily understood when the following detailed description is considered in conjunction with the accompanying drawings are realized by system for percutaneous myocardial revascularization having a catheter, the catheter having a proximal end and a distal end. The distal end of the catheter includes: an applicator for revascularizing energy operable to revascularize a patient's heart, the revascularizing energy being non-mechanical energy; a navigation device operable to provide sensing of the position of the distal end and having wires carrying navigation signals (i.e., signals depending on the position and/or orientation of the navigation device) from the navigation device to the proximal end; and a pressure sensor operable to sense ventricular pressure during revascularization of a patient's heart. As used herein, non-mechanical energy would include any energy which creates a new vascular channel without mechanically cutting, drilling, poking, abrading and, more generally without otherwise using movement of a solid member or members into patient tissue such that the movement of the solid member(s) into the tissue creates the new vascular channel. Such nonmechanical energy would include, among others, energy in the following forms: laser, radio frequency, heat, ultrasonic, high pressure fluid, and, more generally, other forms of electromagnetic energy.

More specifically, the applicator applies electromagnetic energy. Even more specifically, the applicator applies laser energy.

An embodiment has an applicator which includes a beam controller operable to receive the laser energy and selectively direct it in different directions. Another embodiment uses an applicator which applies laser energy in the form of a plurality of beams.

The navigation device is operable to provide sensing of the position of the distal end by use of magnetic fields. The navigation device includes two non-coplanar magnetic elements. The system further includes a plurality of external magnetic elements for placement outside of the patient and a computer operably connected to the plurality of external magnetic elements and operably connected to the navigation device. The computer is operable to sense the position of the distal end by way of magnetic field interaction between the plurality of external magnetic elements and the navigation device. The external magnetic elements establish magnetic fields which are sensed by the navigation device.

The present invention may alternately be described as a system for percutaneous myocardial revascularization having a catheter. The catheter has a proximal end and a distal end. The distal end of the catheter includes: an applicator for applying revascularizing laser energy operable to revascularize a patient's heart; and a navigation device operable to provide sensing of the position of the distal end using magnetic fields. The navigation device is a sensor operable to sense magnetic fields. The navigation device includes two non-coplanar magnetic elements.

The system further includes a plurality of external magnetic elements for placement outside of the patient and a computer operably connected to the plurality of external magnetic elements and operably connected to the navigation device. The computer is operable to sense the position of the distal end by way of magnetic field interaction between the plurality of external magnetic elements and the navigation device. The plurality of external magnetic elements establish magnetic fields which are sensed by the navigation device. The plurality of external magnetic elements establish different magnetic fields sequentially, the navigation device is operable to sense the different fields, and the computer is operable to determine distal end position by comparing the sensed fields with a known sequence of establishing the different magnetic fields. The plurality of external magnetic elements are three sets of three coils, each set of three coils being sequentially energized.

The distal end includes a side wall with a hole therein and the applicator includes a lens directing laser energy out the hole.

The method of the present invention may be described as treating a patient by the steps of: percutaneously inserting a catheter in a patient, the catheter having a proximal end and a distal end; sensing the position of the distal end using magnetic fields and a navigation device in the distal end; positioning the catheter such that its distal end is adjacent patient tissue which is to be revascularized; applying revascularizing energy from an applicator disposed at the distal end to the patient tissue, the revascularizing energy being non-mechanical energy; and sensing pressure at the distal end using a pressure sensor in the distal end.

The method of the present invention may alternately be described as treating a patient by the steps of: percutaneously inserting a catheter in a patient, the catheter having a proximal end and a distal end; sensing the position of the distal end using magnetic fields and a navigation device in the distal end; positioning the catheter such that its distal end is adjacent heart tissue which is to be revascularized; and applying revascularizing laser energy from an applicator disposed at the distal end to the heart tissue, the revascularizing energy being non-mechanical energy.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
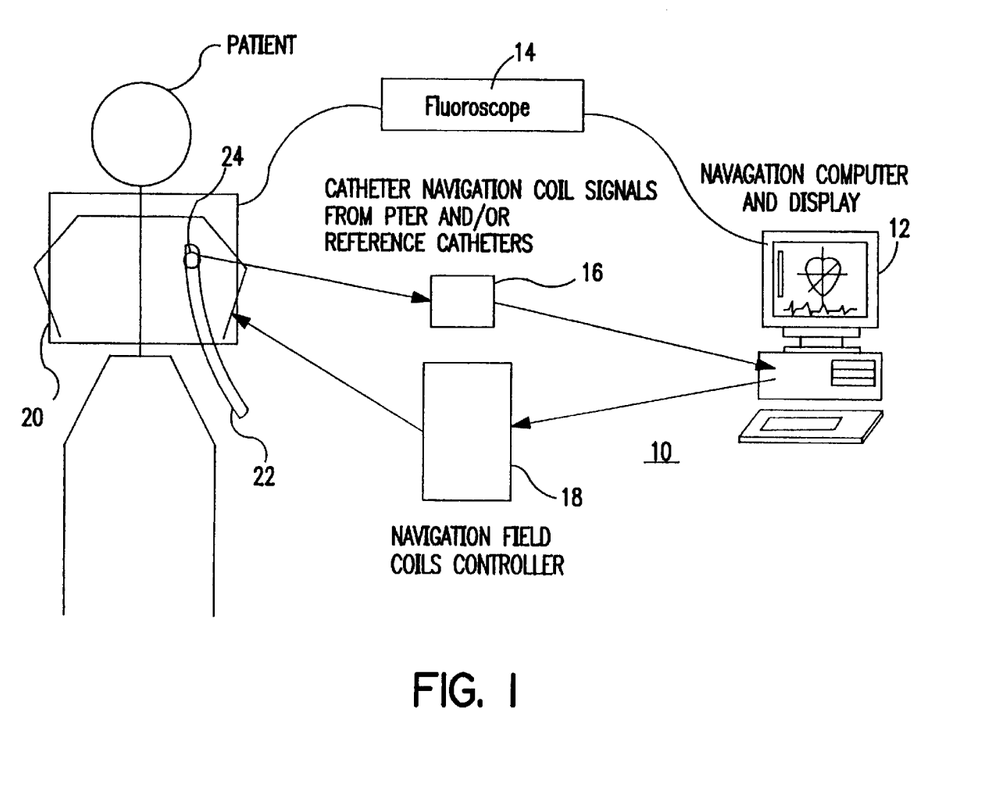
FIG. 1 is a simplified diagram of a patient and various components of a first system of the present invention.

With reference now to the simplified diagram of FIG. 1, a first system 10 according to the present is shown together with a patient represented in stick form. The part of the patient's heart which needs revascularization can be identified using ultrasound, a positron emission tomography (PET) scanning, magnetic resonance imaging (MRI), scintegraphy, echocardiography, or other appropriate imaging technique. The system includes a computer 12 which displays images of one of several stored heart images which are more or less standard images. In particular, the computer 12 will have various heart images stored therein and a doctor or other medical worker can select one of the images. The selected image will be that which is thought to most closely resemble a particular patient's heart and the computer can scale the size of the image (after the medical worker has provided reference points from measurements with the patient's heart) so that dimensions on the display are consistent with the size of the particular patient's heart. Alternately, or additionally, a fluoroscope 14 or other imaging system (such as those mentioned above as used for finding the part of the patient's heart which needs revascularization) can provide an image of the patient either to a different display (not shown) or to the display of computer 12. In the latter case, the computer display may show two images at once and/or be switchable between the images.

If desired, data from any previously or concurrently performed fluoroscope, ultrasound, a positron emission tomography (PET) scanning, magnetic resonance imaging (MRI), scintegraphy, echocard(ography, or other appropriate imaging technique can be integrated into the image as displayed based on the stored standard heart image. Alternately or additionally, images from concurrently or previously performed fluoroscope, ultrasound, a positron emission tomography (PET) scanning, magnetic resonance imaging (MRI), scintegraphy, echocardiography, or other appropriate imaging technique can be displayed and used for integrating navigation data (navigation data is discussed in detail below) therein. That is, if the use of stored heart images which are more or less standard images is unacceptable in a particular situation, images based on actual patient data without reference to standard images could be used.

A junction box 16 forwards sensed signals to the computer corresponding to magnetic fields established by a coil controller 18 selectively and sequentially energizing (under control of computer 12) sets of external (i.e., external to the patient) coils 20 (shown as a box only). A catheter 22 with its distal end inside the heart of the patient has a navigation device 24 which senses the magnetic fields established by the external coils 20. The computer considers the known sequence of energizing of the coils 20 and the sensed magnetic fields and then calculates relatively precisely the position of the distal end of the catheter 22. The junction box may also optionally forward any signals from reference catheters (not shown), which reference catheters may have navigation devices like 24 and which may be used simply to avoid having device 24 show position fluctuations due to movement of the patients heart and/or chest. In other words, computer 12 will best illustrate the position of the distal end relative to the patient's heart if a movement of the device 24 with the heart is not shown as a movement of the device 24.

When the distal end of catheter 22 is properly positioned relative to ischemic portions of a patient's ventricle or other tissues of the patient which require revascularization, the catheter applies revascularizing energy to the tissue in a manner discussed in detail below.

Figure 2:
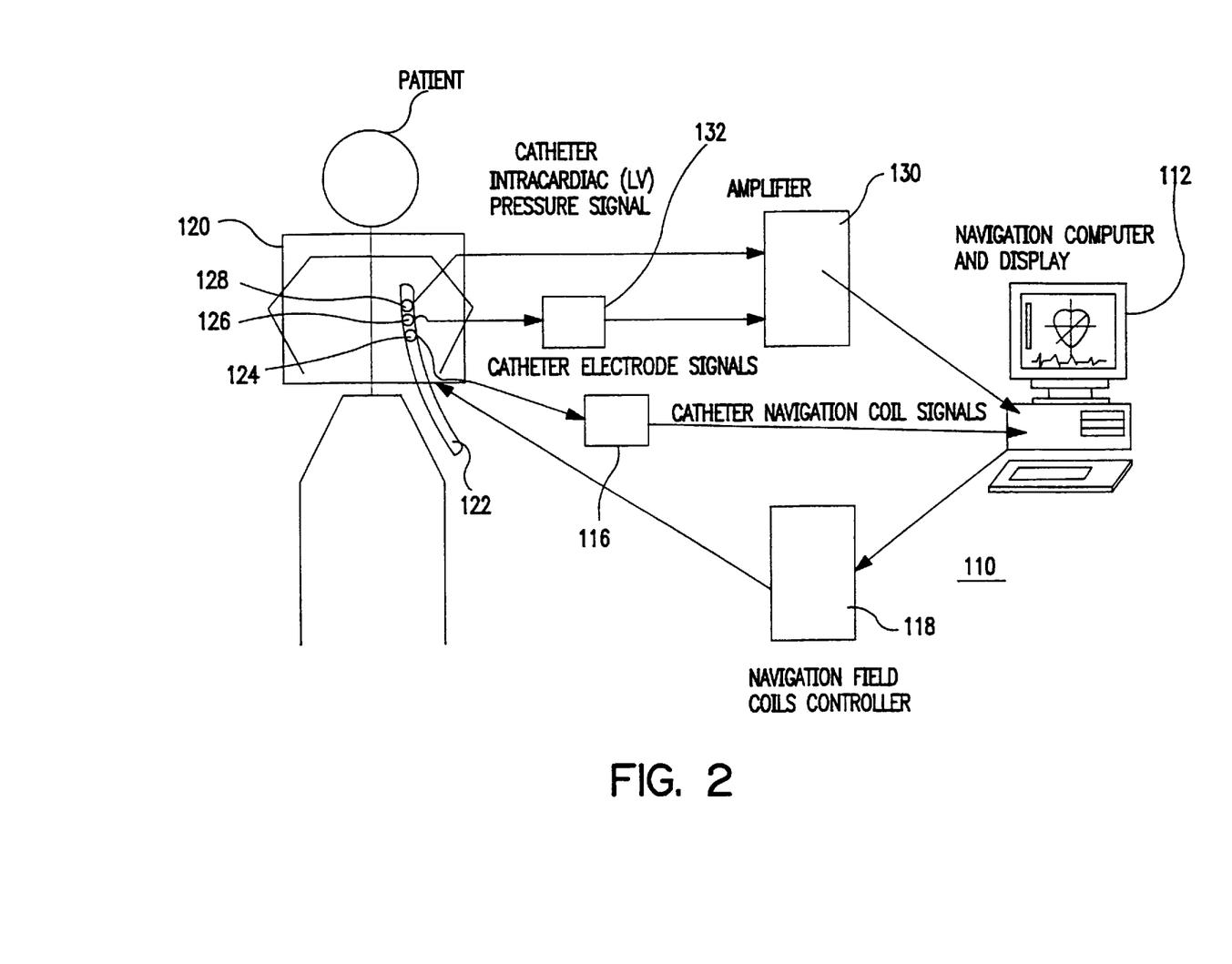
FIG. 2 is a simplified diagram of a patient and various components of a second system of the present invention.

With reference now to the simplified diagram of FIG. 2, a second system 110 according to the present is shown together with a patient represented in stick form. The system 110 has components in the 100 series with the same last two digits as the corresponding component, if any, from the system of FIG. 1. Thus, computer 112, junction box 116, coil controller 118, external field coils 120, catheter 122, and navigation device 124 function and are arranged the same as corresponding components in FIG. 1 except for any differences noted hereafter. A fluoroscope is not shown in FIG. 2 for ease of illustration, but one could be used in FIG. 2 in the same fashion as shown and described relative to FIG. 1.

Some additional features and components of the FIG. 2 embodiment will now be discussed. The catheter 122 has electrodes 126 which sense the impedance in the heart and pressure sensor 128 which senses the intracardiac left ventricle pressure. Signals from 126 and 128 are relayed to computer 112 via amplifier 130, signals from 126 initially passing through junction box 132. The electrodes 126 may help to confirm proper positioning of the catheter. The sensor 128 will warn medical personnel if the left ventricle pressure rises too high, which condition is indicative of problems from the revascularization.

The construction of catheter 122 will be discussed with reference to FIG. 3, whereas it will be understood that catheter 22 of FIG. 1 would be constructed in identical fashion except without components 126 and 128 (including the parts of these components). Catheter 122 includes an inner catheter portion 132 having distal and proximal ends 132D and 132P respectively, an outer catheter portion 134 having distal and proximal ends 134D and 134P respectively, spring 136, optical fiber 138, laser 140, and connector 142, all of which are constructed and function in the same fashion as components identified and described in detail in the incorporated by reference 5,464,404 patent. (Moreover, additional features disclosed in that patent relative to different constructions for the inner catheter portion and relative to other features may be combined with the present catheter.) Beyond a brief description of those common components, only differences from the '404 design will be discussed. The spring 136 allows one to anchor portion 134A in the patient's heart such that outer catheter portion 134 is anchored in position, while the inner catheter 132 may be moved relative thereto for applying laser energy against heart tissue.

Among differences relative to the catheter of the '404 design, the laser beam 144L from hole 144 (which also allows exit of flushing solution 144F) in the side wall of catheter portion 132 may have different characteristics as discussed below to provide for revascularization as opposed to the ablation of ventricular arrhythmia foci (which purpose was the primary emphasis of the '404 patent). The electrodes 126F, 126S, and 126T are optional and may be used to insure that the catheter is properly stabilized within the heart and/or to differentiate types of heart tissue.

Unlike the catheter in the '404 patent, the catheter 122 has the intracardiac left ventricle pressure sensor 128 which detects if the pressure rises too high, thus indicating danger. Sensor 128 may be an electronic sensor with signal carrying wires 128W (FIG. 4 only) extending to the proximal end. (The carried signals indicate the sensed pressure.) Alternately, the sensor could be a fluid type pressure sensor.

Figure 4:
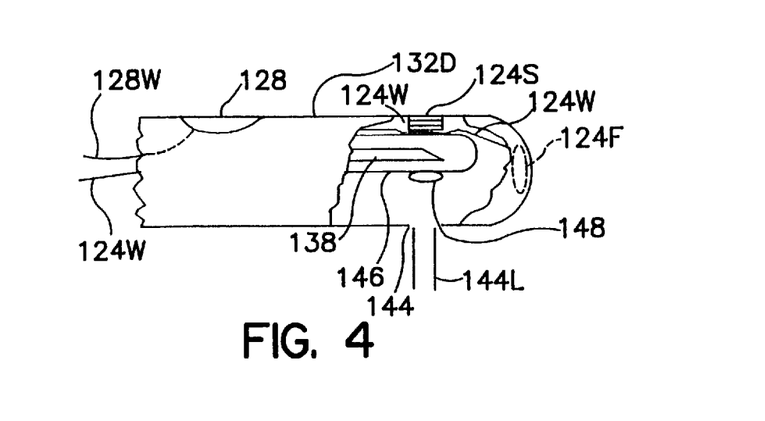
FIG. 4 is a detailed side view, with a portion removed, of the distal tip of the first embodiment catheter.

With reference now to FIG. 4, details of the distal end of catheter portion 132D will be discussed. For ease of illustration, the optional electrodes 126F and 126S are not shown in FIG. 4. The optical fiber 138 ends within an inner hood 146 and outer hood (corresponding to the distal most portion of 132D). The construction details of the inner and outer hoods are disclosed in the incorporated by reference 5,061,265 patent. A lens 148 is attached to inner hood 146 in order to better collimate the beam 144L. Drop offs in laser energy density, which are acceptable for ablation purposes, may not be acceptable in revascularization. Lens 148 helps minimize thermal injury to tissue by maintaining high energy density.

Figure 3:
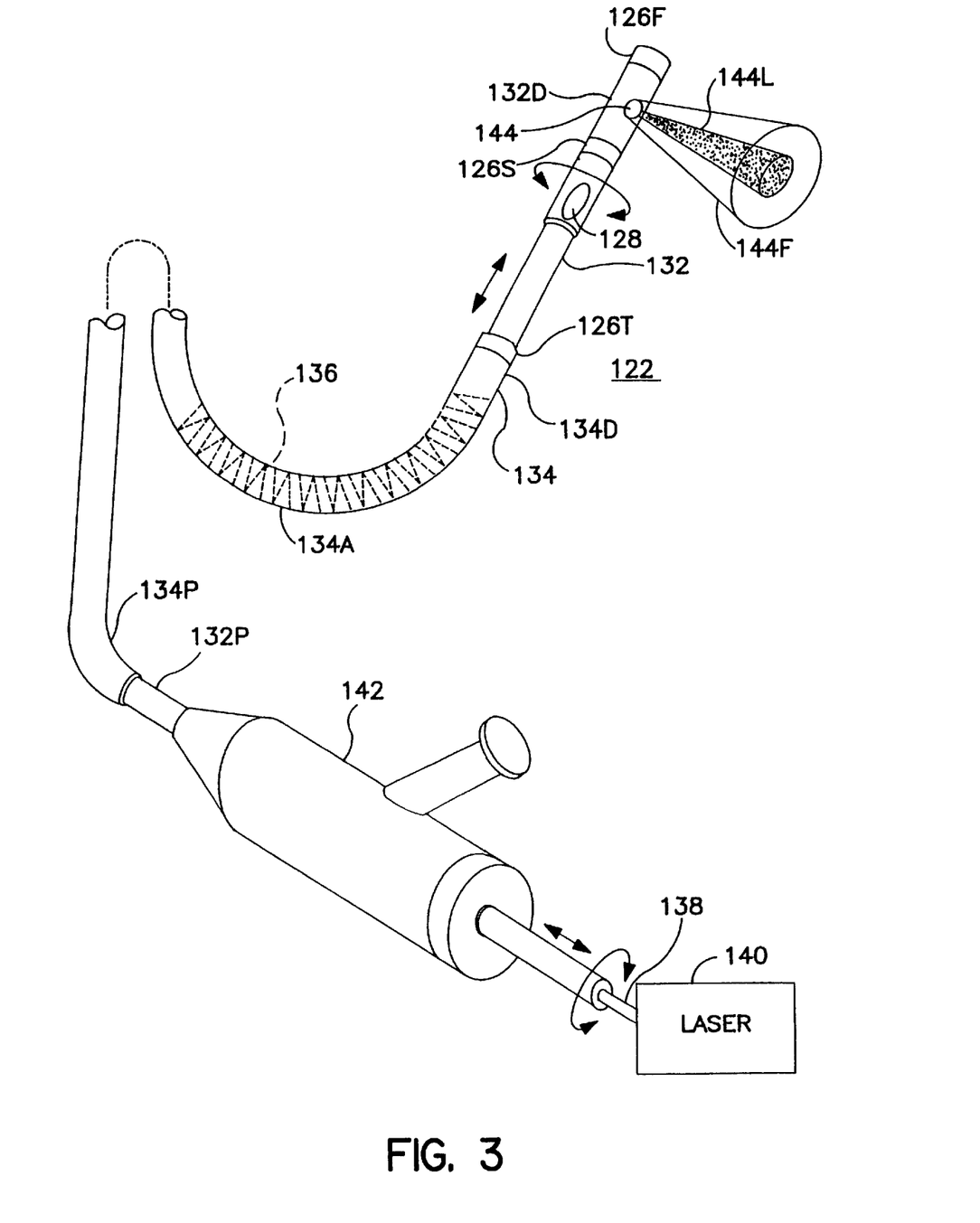
FIG. 3 is perspective view of a first embodiment catheter of the present invention.

The navigation device 124 of FIG. 2 was not shown in FIG. 3, but is shown as first and second non-coplanar magnetic sensing coils 124F and 124S respectively, both of which have wires 124W carrying navigation signals to the proximal end of the catheter.

Figure 5:
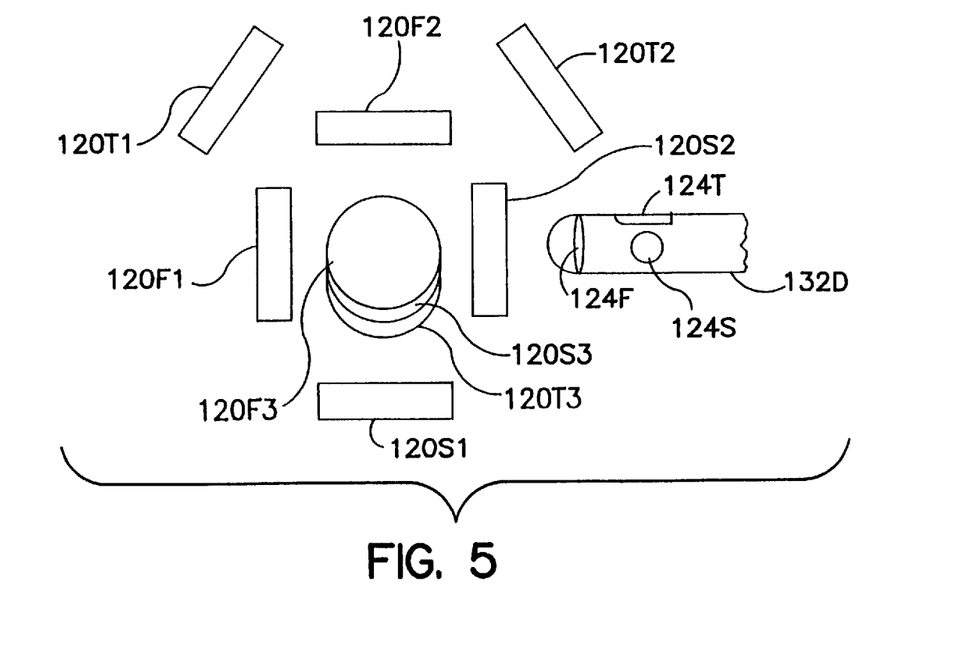
FIG. 5 is a diagram of a navigation subsystem of the present invention.

The navigation subsystem is illustrated in FIG. 5 as having a first set of three orthogonal external coils 120F1, 120F2, and 120F3, a second set of three orthogonal external coils 120S1, 120S2, and 120S3, and a third set of three orthogonal external coils 120T1, 120T2, and 120T3. The three sets collectively make up the external field coils 120 of FIG. 2. For ease of illustration, coils 120F3, 120S3, and 120T3 are shown as all being in planes parallel to the plane of view of FIG. 5. However, different arrangements could be used. In the same sense that 120F1 establishes a magnetic field extending primarily left to right relative to FIG. 5 and coil 120T1 establishes a magnetic field extending primarily diagonally, one may use an arrangement in which no two of the coils establish a field with the same primary direction. Thus, different orientations for the various coils and/or different positioning arrangements could be used.

The controller 118 (FIG. 2 only) sequentially energizes the external coils with the patient adjacent thereto, one at a time, such that sensing coils such as 124F, 124S, and 124T on the distal end 132D of the catheter within the patient senses the established magnetic fields. The computer 112 (FIG. 2) considers the known sequence of energizing of the external coils and the sensed magnetic fields and then calculates relatively precisely the position of the distal end 132D of the catheter. As will be readily appreciated the position calculation is made relative to the external coils such as 120F1, etc. Those coils therefore will be readily understood as establishing a frame of reference external to the patient.

Although FIG. 4 illustrates three of the sensing coils 124F, 124S, and 124T serving as navigation device 124 of FIG. 2, a single sensing coil or other magnetic element (i.e., magnetic sensing or generating device) may be used for a five degree of freedom sensing of the distal end. In other words, a single sensor can give x, y, and z position information and two of three orientation angles relative to the distal end. Two or more such sensors provide six degree of freedom (x, y, and z position information and all three orientation angles) navigation. Using more than two sensors creates redundancy and may provide greater accuracy and/or a higher confidence level in the information.

Although the external magnetic elements 120 have been shown as the three sets of coils (which may be two lead magnet wire coils), other techniques could alternately be used to generate magnetic fields. Among such techniques, mechanical rotation and/or translation of permanent magnets or DC electromagnets or magnetic fields from magnetic resonance imaging (MRI) systems could be used. Indeed, any arrangement of magnetic field generators that yield a unique set of field measurements for any position and orientation will work. One could energize a single one of the coils at a time. In any case, each sensing coil of the navigation device 124 generates a signal in response to the generated magnetic fields and dependent on the location of the sensing coil relative to the generating coil. The sensed signals are fed to the computer which uses the data to solve field coupling equations and determine a position and orientation in space of the distal end of the catheter. The computer then may associate this data point with the optional cardiac potential obtained at that location. The computer is also programmed to incorporate the position and orientation into the heart display described above.

As an alternative to sequentially energizing each of the external coils, all external coils could be energized at a time, but at different frequencies and/or phases.

Additionally and/or alternately to the previously mentioned optional reference catheters (which may be in the right side chambers or other suitable areas of the heart), a skin patch may be used to provide a reference coordinate system accounting for patient movement and respiration.

Although the magnet elements 124F, 124S, and 124T have been described as sensing coils such as two lead wound magnet wire coils, alternative magnet elements could be used. Among alternatives are two lead resonated wound magnet wire coils, four lead semiconductor hall effect device or devices in a bridge configuration, two lead semiconductor magneto-resistive device or devices in a bridge configuration, a saturated core flux gate magnetometer, two lead wound magnet wire coil wound around a saturable core, a micro-machined vibrating cantilever with an attached two lead wound magnet wire coil, and electron tunneling magnetometer, or a giant magnetoresistance ratio (GMR) sensor or sensors in a bridge configuration mounted on the distal tip of the catheter.

Preferably the magnet elements in the catheter are for sensing and the external magnet elements generate magnetic fields, but the magnet elements in the catheter could generate the fields and the external magnet elements could sense the magnetic fields. A magnet, either fixed or moving rotationally or translationally, could be in the catheter to generate a magnetic field.

Figure 6:
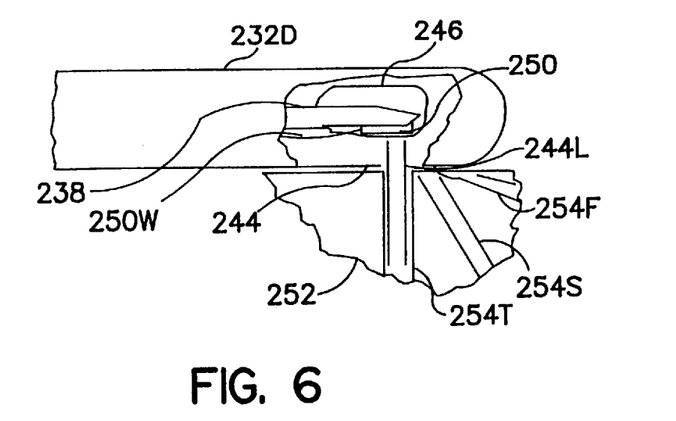
FIG. 6 is a detailed side view, with a portion removed, of the distal tip of a second embodiment catheter.

FIG. 6 shows a second embodiment distal end 232D of a catheter with components in the 200 series with the same last two digits as the corresponding component, if any, from the catheters of FIGS. 1–5. Thus, optical fiber 238, hole 244, and inner hood function and are arranged the same as corresponding components in FIGS. 1–5 except for any differences noted hereafter. The embodiment of FIG. 6 uses an acousto-optic coupler 250 (controlled from the proximal end by electrical signals on wires 250 W) as a beam controller to electronically steer laser beam 244L out of hole 244 at different angles. The acousto-optic coupler 250 allows laser cutting of first, second, and third (for example) channels 254F, 254S, and 254T in heart tissue 252 without moving the inner catheter portion. A pattern of channels similar to branches from a bush may be created. Depending on the condition and shape of disease tissue establishing such a pattern of diverging channels may be useful.

Figure 7:
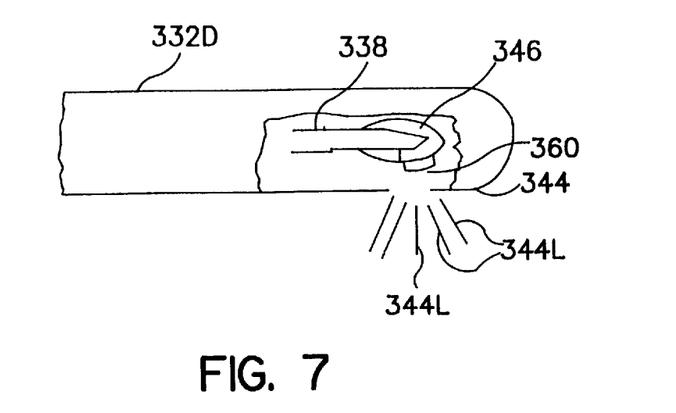
FIG. 7 is a detailed side view, with a portion removed, of the distal tip of a third embodiment catheter.

FIG. 7 shows a third embodiment distal end 332D of a catheter with components in the 300 series with the same last two digits as the corresponding component, if any, from the catheters of FIGS. 1–5. Thus, optical fiber 338, holes 344, and inner hood 346 function and are arranged the same as corresponding components in FIGS. 1–5 except for any differences noted hereafter. The embodiment of FIG. 7 is different than the other embodiments in that a plurality of holes 344 are in the side wall of the catheter to create a plurality of beams 344L such that a plurality of channels may be lased at a given time. The construction details of an arrangement to provide a plurality of beams is disclosed in U.S. Pat. No. 5,246,437 issued Sep. 21, 1993 to Abela and hereby incorporated by reference. The beams from distal end 332D may have the characteristics of the beams disclosed in that patent or may be larger beams. The condition of the diseased tissue and other factors may influence the desirable width for the beams 344L. Optionally, a diverging lens 360 may spread the beam before it is divided into multiple beams by the array of holes 344. In that fashion, the beams 344L may fan out from a common source point with the same pattern as in FIG. 6.

The FIGS. 6 and 7 embodiments would have the navigation device and, optionally, electrode arrangements as previously discussed, but those components are not shown in these FIGS. for ease of illustration.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A system for percutaneous myocardial revascularization comprising a catheter, the catheter having a proximal end and a distal end, the distal end of the catheter including:
    an applicator for revascularizing energy operable to revascularize a patient's heart by creating holes partly through a wall of the heart, the revascularizing energy being non-mechanical energy;
    a navigation device operable to provide sensing of the position of the distal end and having wires for carrying navigation signals between the navigation device and the proximal end, the navigation device referencing the distal end relative to a frame of reference external to the patient; and
    a pressure sensor operable to sense ventricular pressure during revascularization of a patient's heart.

2. The system for percutaneous myocardial revascularization of claim 1 wherein the applicator applies electromagnetic energy.

3. The system for percutaneous myocardial revascularization of claim 2 wherein the applicator applies laser energy.

4. The system for percutaneous myocardial revascularization of claim 3 wherein the applicator includes a beam controller operable to receive the laser energy and selectively direct it in different directions.

5. The system for percutaneous myocardial revascularization of claim 3 wherein the applicator applies laser energy in the form of a plurality of beams.

6. The system of claim 3 wherein the catheter includes an outer catheter and an optical fiber for carrying the revascularizing laser energy, the optical fiber slidably mounted relative to the outer catheter.

7. The system for percutaneous myocardial revascularization of claim 6 wherein the navigation device includes a magnetic element and further comprising a plurality of external magnetic elements for placement outside of the patient and a computer operably connected to the plurality of external magnetic elements and operably connected to the navigation device, and wherein the computer is operable to sense the position of the distal end by way of magnetic field interaction between the plurality of external magnetic elements and the navigation device.

8. The system for percutaneous myocardial revascularization of claim 1 wherein the navigation device is operable to provide sensing of the position of the distal end by use of magnetic fields.

9. The system for percutaneous myocardial revascularization of claim 8 wherein the navigation device includes two non-coplanar magnetic elements.

10. The system for percutaneous myocardial revascularization of claim 8 further comprising a plurality of external magnetic elements for placement outside of the patient and a computer operably connected to the plurality of external magnetic elements and operably connected to the navigation device, and wherein the computer is operable to sense the position of the distal end by way of magnetic field interaction between the plurality of external magnetic elements and the navigation device.

11. The system for percutaneous myocardial revascularization of claim 10 wherein the external magnetic elements establish magnetic fields which are sensed by the navigation device.

12. The system for percutaneous myocardial revascularization of claim 8 wherein the applicator applies laser energy and the navigation device is a sensor operable to sense magnetic fields.

13. The system of claim 1 wherein the catheter includes an outer catheter and an optical fiber slidably mounted relative to the outer catheter.

14. A system for percutaneous myocardial revascularization comprising a catheter, the catheter having a proximal end and a distal end, the distal end of the catheter including:
    an applicator for applying revascularizing energy operable to revascularize a patient's heart by creating holes partly through a wall of the heart, the revascularizing energy being non-mechanical energy; and
    a navigation device operable to provide sensing of the position of the distal end using magnetic fields, the navigation device referencing the distal end relative to a frame of reference external to the patient.

15. The system for percutaneous myocardial revascularization of claim 14 wherein the applicator applies revascularizing laser energy.

16. The system for percutaneous myocardial revascularization of claim 15 wherein the navigation device is a sensor operable to sense magnetic fields.

17. The system for percutaneous myocardial revascularization of claim 15 wherein the navigation device includes two non-coplanar magnetic elements.

18. The system for percutaneous myocardial revascularization of claim 15 further comprising a plurality of external magnetic elements for placement outside of the patient and a computer operably connected to the plurality of external magnetic elements and operably connected to the navigation device, and wherein the computer is operable to sense the position of the distal end by way of magnetic field interaction between the plurality of external magnetic elements and the navigation device.

19. The system for percutaneous myocardial revascularization of claim 18 wherein the plurality of external magnetic elements establish magnetic fields which are sensed by the navigation device.

20. The system for percutaneous myocardial revascularization of claim 19 wherein the plurality of external magnetic elements establish different magnetic fields sequentially, the navigation device is operable to sense the different fields, and the computer is operable to determine distal end position by comparing the sensed fields with a known sequence of establishing the different magnetic fields.

21. The system for percutaneous myocardial revascularization of claim 20 wherein the plurality of external magnetic elements are three sets of three coils, each set of three coils being sequentially energized.

22. The system for percutaneous myocardial revascularization of claim 15 wherein the distal end includes a side wall with a hole therein and the applicator includes a lens directing laser energy out the hole.

23. The system for percutaneous myocardial revascularization of claim 15 wherein the applicator includes a beam controller operable to receive the laser energy and selectively direct it in different directions.

24. The system for percutaneous myocardial revascularization of claim 15 wherein the applicator applies laser energy in the form of a plurality of beams.

25. The system of claim 15 wherein the catheter includes an outer catheter and an optical fiber for carrying the revascularizing laser energy, the optical fiber slidably mounted relative to the outer catheter.

26. The system for percutaneous myocardial revascularization of claim 25 wherein the navigation device includes a magnetic element and further comprising a plurality of external magnetic elements for placement outside of the patient and a computer operably connected to the plurality of external magnetic elements and operably connected to the navigation device, and wherein the computer is operable to sense the position of the distal end by way of magnetic field interaction between the plurality of external magnetic elements and the navigation device.

27. The system of claim 14 wherein the catheter includes an outer catheter and an optical fiber slidably mounted relative to the outer catheter.

28. A method of treating a patient comprising the steps of;
   percutaneously inserting a catheter in a patient, the catheter having a proximal end and a distal end;
   sensing the position of the distal end using magnetic fields and a navigation device in the distal end;
   using the navigation device to reference the distal end relative to a frame of reference external to the patient
   positioning the catheter such that its distal end is adjacent patient tissue which is to be revascularized;
   applying revascularizing energy from an applicator disposed at the distal end to the patient tissue, the revascularizing energy being non-mechanical energy which creates holes partly through a wall of the heart; and
   sensing pressure at the distal end using a pressure sensor in the distal end.

29. The method of claim 28 wherein the applying step includes applying revascularizing laser energy to the heart tissue.

30. The method of claim 29 wherein the catheter includes an outer catheter and an optical fiber slidable within the outer catheter, and, prior to the applying of revascularizing laser energy, the optical fiber is slid in a distal direction relative to the outer catheter.

31. The method of claim 30 wherein the catheter further includes an inner catheter and the optical fiber is mounted in the inner catheter such that the optical fiber and inner catheter are slidable together within the outer catheter, and, prior to the applying of revascularizing laser energy, the inner catheter and optical fiber are slid together in a distal direction relative to the outer catheter.

32. A method of treating a patient comprising the steps of:
   percutaneously inserting a catheter in a patient, the catheter having a proximal end and a distal end;
   sensing the position of the distal end using magnetic fields and a navigation device in the distal end, the navigation device referencing the distal end relative to a frame of reference external to the patient;
   positioning the catheter such that its distal end is adjacent heart tissue which is to be revascularized; and
   applying revascularizing energy from an applicator disposed at the distal end to the heart tissue, the revascularizing energy being non-mechanical energy which creates holes partly through a wall of the heart.

33. A method of claim 32 wherein the applying step includes applying revascularizing laser energy to the heart tissue.

34. The method of claim 33 wherein the catheter includes an outer catheter and an optical fiber slidable within the outer catheter, and, prior to the applying of revascularizing laser energy, the optical fiber is slid in a distal direction relative to the outer catheter.

35. The method of claim 34 wherein the catheter further includes an inner catheter and the optical fiber is mounted in the inner catheter such that the optical fiber and inner catheter are slidable together within the outer catheter, and, prior to the applying of revascularizing laser energy, the inner catheter and optical fiber are slid together in a distal direction relative to the outer catheter.

* * * * *